United States Patent [19]

Zaiko

[11] 4,246,176
[45] Jan. 20, 1981

[54] SYNTHESIS OF 5-AROYL-1-HYDROCARBYLPYRROLE-2-ACETIC ACID

[75] Inventor: Edward J. Zaiko, Baton Rouge, La.

[73] Assignee: Ethyl Corporation, Richmond, Va.

[21] Appl. No.: 55,039

[22] Filed: Jul. 5, 1979

[51] Int. Cl.$^3$ .................................... C07D 207/337
[52] U.S. Cl. ...................... 260/326.47; 260/326.2; 424/274
[58] Field of Search ................................ 260/326.47

[56] References Cited

U.S. PATENT DOCUMENTS

| | | | |
|---|---|---|---|
| 3,846,447 | 11/1974 | Carson | 260/326.47 |
| 3,952,012 | 4/1976 | Carson | 260/326.47 |
| 4,048,191 | 9/1977 | Carson | 260/326.47 |
| 4,119,639 | 10/1978 | Carson | 260/326.47 |

OTHER PUBLICATIONS

Müller, Methoden der Organischen Chemie, vol. 7/2a, p. 616, (1973).

Kharasch et al., "Grignard Reactions of Non-Mettalic Substances", 767–845, 948–960, (1954).

Primary Examiner—Mary C. Lee
Attorney, Agent, or Firm—Donald L. Johnson; John F. Sieberth

[57] ABSTRACT

The reaction between a 5-cyano-1-hydrocarbylpyrrole-2-acetic acid and an aryl Grignard compound to produce a ketimine salt-containing reaction intermediate is improved by performing such reaction in an aromatic ether reaction medium at a temperature above about 100° C. As compared to the previously known process, the reaction rate is markedly increased without loss of selectivity. Also, the water insolubility of aromatic ethers simplifies product work-up and recovery, reduces product losses, and facilitates solvent recovery and recycle. Preferably, the aryl Grignard reagent is prepared at the outset in tetrahydrofuran or methyl tetrahydrofuran—solvents in which such Grignard reagents are readily and safely produced. The resultant Grignard solution may then be employed in forming the aromatic ether-containing reaction medium in which the above reaction is conducted.

22 Claims, No Drawings

SYNTHESIS OF 5-AROYL-1-HYDROCARBYLPYRROLE-2-ACETIC ACID

INTRODUCTION

This invention relates to a method for the synthesis of 5-acyl-1-hydrocarbylpyrrole-2-acetic acids and more particularly, 5-aroyl-1-hydrocarbylpyrrole-2-acetic acids.

BACKGROUND

A wide variety of 5-acyl-1-hydrocarbylpyrrole-2-acetic acids are known to possess useful pharmacological properties. For example, 1-methyl-5-p-toluoylpyrrole-2-acetic acid has a marked anti-inflammatory activity [J. Pharmacology and Experimental Therapeutics, 185, 127 (1973)]. See also U.S. Pat. Nos. 3,752,826; 3,755,307; 3,803,169; 3,803,171 and 4,048,191 (the disclosures of which are incorporated herein) which describe, inter alia, numerous 5-acyl-1-hydrocarbylpyrrole-2-acetic acids having anti-inflammatory and analgetic activities.

In copending application Ser. No. 963,673, filed Nov. 27, 1978 (the disclosure of which is incorporated herein), Kondo, Suda and Tunemoto describe a novel and useful process for producing 5-acyl-1-hydrocarbylpyrrole-2-acetic acid. In that process, a 5-cyano-1-hydrocarbylpyrrole-2-acetic acid is reacted with a Grignard compound and then the resultant reaction product is hydrolyzed. The use of solvents is preferred and examples of the solvent used in the Kondo et al. acylation process are ethers such as ether, dioxane, tetrahydrofuran, dimethoxyethane and the like or hydrocarbons containing organic tertiary amines. A Grignard reagent is prepared in these solvents and then the 5-cyano-1-hydrocarbylpyrrole-2-acetic acid is added. The reaction can preferably be carried out at room temperature or at a reflux temperature of the solvent used. Preferably, the Grignard reagent is used in an amount of more than two molar equivalents. One molar equivalent of Grignard reagent is consumed for the production of carboxylic acid salt and the balance is used for the introduction of the acyl group.

The reaction mixture formed in the Kondo et al. acylation process is worked up and then hydrolyzed. The hydrolysis can be accomplished by the direct addition of acidic substances such as hydrochloric acid, sulfuric acid, phosphoric acid, oxalic acid, aqueous ammonium chloride and the like. From the standpoint of the reaction mechanism, the reaction is deemed to proceed via the formation of a ketimine salt as an intermediate.

Although the foregoing process of Kondo et al. is a significant contribution to the art, it nonetheless is not without its shortcomings. In particular, to achieve optimum yields, relatively long reaction periods have been used. In practical short reaction times the reaction was found to have occurred only to a limited extent—a substantial amount of unreacted cyano acid starting material was recoverable from the reaction mixture even though the reaction system contained a substantial excess of the Grignard reagent. For instance, in their Example 8, 1-methyl-5-p-toluoylpyrrole-2-acetic acid was produced in a yield of about 63.5% based on the 5-cyano-1-methylpyrrole-2-acetic acid reactant employed, after a reaction period at reflux of two hours. On the other hand, in their Example 9 this product was formed in an 84% yield based on the initial cyano acid, but in this case, a 21-hour reflux reaction period was involved. Obviously, long reaction periods such as this severely curtail productivity and add significantly to plant and operating costs.

THE INVENTION

An improvement in the Kondo et al. procedure for producing 5-acyl-1-hydrocarbylpyrrole-2-acetic acid has now been discovered. This improved process enables the reaction to be carried out with good yields in short reaction periods, oftentimes in two hours or less. In addition, it has been found possible to perform this reaction effectively when employing the cyano acid reactant in various forms—viz., in the form of the free acid itself, as an alkali metal salt of the acid, and as a calcium salt of the acid.

In accordance with this invention, the Kondo et al. acylation process for preparing 5-aroyl-1-hydrocarbylpyrrole-2-acetic acid is improved in that the reaction between the cyano acid and the aryl Grignard compound is performed at a temperature above about 100° C. in a liquid ether reaction medium consisting essentially of an aromatic ether. Optionally, and preferably, tetrahydrofuran or methyl tetrahydrofuran, or both of these are also present in the liquid ether reaction medium. That is, a preferred embodiment involves performing the foregoing reaction at a temperature above about 100° C. in a liquid ether reaction medium consisting essentially of (i) an aromatic ether and (ii) tetrahydrofuran or methyl tetrahydrofuran, or both.

By employing an aromatic ether (either alone or in combination with tetrahydrofuran or methyl tetrahydrofuran or both), not only is it possible to perform the reaction at an elevated temperature at which the reaction rate is rapid, but the selectivity of the reaction is not appreciably impaired—i.e., by conducting the reaction at an appropriate reaction temperature, it is possible to avoid the formation of excessive amounts of undesired by-products and decomposition products. Furthermore, aromatic ethers tend in general to be good solvents for the aryl Grignard reagents and thus facilitate the reaction of the Grignard reagent with the cyano acid co-reactant. Moreover, unlike such ethers as dioxane, dimethoxyethane, and the like, aromatic ethers generally have very low water solubilities and this simplifies subsequent product work-up and recovery, reduces product losses and facilitates solvent recovery and recycle.

A further advantage is that the aryl Grignard reagent can be and preferably is prepared at the outset in tetrahydrofuran or methyl tetrahydrofuran—solvents in which such Grignard reagents are readily and safely produced. Combining the resultant Grignard solution with a higher boiling aromatic ether makes it possible to perform the reaction in the mixed solvent at an elevated temperature above the normal boiling points of these tetrahydrofuran solvents. And since these tetrahydrofuran solvents have relatively low boiling points (tetrahydrofuran 65° C., 2-methyltetrahydrofuran 78°–80° C., 3-methyltetrahydrofuran 86°–87° C.) they can readily be distilled from the reaction system for recovery and recycle, should this be desired.

It has also been found that the facility with which the aryl Grignard reagent can be prepared in tetrahydrofuran manifests itself when synthesizing the aryl Grignard reagent in a mixture of the tetrahydrofuran with a suitable aromatic ether such as anisole. Thus, another embodiment of this invention involves preparing the Grignard reagent at the outset in an ether reaction medium consisting essentially of a mixture of an aromatic ether and tetrahydrofuran or methyl tetrahydrofuran, or both.

It will be seen that when aryl Grignard reagent is synthesized in tetrahydrofuran or methyl tetrahydrofuran, either alone or in admixture with an aromatic ether, the resultant reaction solution may then be employed in forming the reaction mixture in which the aryl Grignard compound and the 5-cyano-1-hydrocarbylpyrrole-2-acetic acid are reacted with each other.

The reaction between the 5-aroyl-1-hydrocarbylpyrrole-2-acetic acid and the aryl Grignard compound may be conducted at any suitable temperature above about 100° C. The reaction rate of course increases with increasing temperature but needless to say, the temperature selected in any given case should not be high enough to cause thermal decomposition of the reactants or products. Reaction temperatures in the range of about 100° to about 150° C. are deemed generally suitable, although use of even higher temperatures than this may be feasible. In the case of reactions involving p-tolyl Grignard reagents, temperatures in the range of about 100° to about 120° C. are preferred, excellent results having been achieved at temperatures of about 110° C. in refluxing diphenyl ether-tetrahydrofuran mixtures. In this connection, it is convenient and desirable, though not essential, to conduct the reaction under reflux since this helps insure that the reaction mixture is well agitated during the reaction—a condition which should be observed for best results. Use in combination of the low boiling tetrahydrofuran or methyltetrahydrofuran together with the high boiling (i.e., above 150° C.) aromatic ethers enables the reaction mixture to be refluxed at any desired temperature in the range of about 100° to about 150° C.

The aromatic ethers employed pursuant to this invention should have sufficient aromaticity in the molecule to dissolve and serve as a good solvent for the aryl Grignard reagents, particularly at the reaction temperatures noted above. The aromatic ethers selected for use should be those which normally exist in the liquid state at the reaction temperature to be used. Preferably, they are liquids even at room temperature as such materials are easier to use than aromatic ethers which are solids at room temperature but liquid at the reaction temperature. It is of course possible to use a mixture of ether solvents, some portion of which is an aromatic ether which normally exists as a solid at the selected reaction temperature provided of course that the mixed solvent is itself liquid at that temperature. However, there is little, if any, advantage in employing such high melting aromatic ethers.

Except for possibly forming soluble ether complexes, the aromatic ether used should be inert to the reactants and reaction product. Thus, besides performing the reaction in an essentially anhydrous system, the aromatic ether(s) used in making up the reaction medium should be free from substituents which would interfere with the desired reaction. These principles of course are well understood to those skilled in the art and should thus not require any further elaboration—suffice it to say that substituents in the aromatic ethers, if any, should be innocuous.

The aromatic ethers, which may be monoethers or polyethers, suitable for use in this invention are exemplified by such materials as the dimethyl ether of hydroquinone, the dimethyl ether of resorcinol, 1,2-dimethoxy benzene, 1,3-diethoxybenzene, ortho-methoxy biphenyl, 3-ethoxybiphenyl, 2,6-dimethoxy toluene, 1-methoxynaphthalene, benzyl ether, and the like. Preferred aromatic ethers are the aryl monoethers in which at least one of the two hydrocarbyl groups attached to the ether oxygen atom is an aryl group, such as phenyl or lower alkyl substituted phenyl groups. One of the hydrocarbyl groups (if both are not aryl) of such aryl monoethers is preferably alkyl, or aralkyl. Naturally, these aryl monoethers are preferably materials which exist in the liquid state at the reaction temperature employed and, most preferably, are those which are also in the liquid state at room temperature. Among the useful aryl monoethers are such substances as diphenyl ether (sometimes known as phenyl ether), anisole, phenetole, butylphenyl ether (butoxy benzene), methoxy-p-tert-amyl benzene, and the like. Diphenyl ether and anisole are particularly preferred because of their commercial availability and relatively low cost.

As noted above, the preferred mixed ether solvent used in the present process includes tetrahydrofuran, methyl tetrahydrofuran or a mixture of these. Because it is widely available at low cost, tetrahydrofuran itself is most preferred for use in this invention. And it is preferred to employ as the mixed ether solvent tetrahydrofuran in combination with one or more of the preferred aryl monoethers described above.

This process is applicable to the use of any of a variety of 5-cyano-1-hydrocarbylpyrrole-2-acetic acids and these may be employed either in the form of the free acid or as an alkali metal salt or as a calcium salt. Generally speaking, it appears that the free acid itself (which presumably is converted in situ into the halomagnesium salt) tends to react somewhat more rapidly than the alkali metal or calcium salt forms and thus from the standpoint of reaction rate, the use of the free cyano acid is preferred.

Methods for preparing the 5-cyano-1-hydrocarbylpyrrole-2-acetic acids are set forth in the foregoing Kondo et al. application. Preferably, however, they are produced by the process described in copending application Ser. No. 43,140, filed May 29, 1979 by Michael J. Dagani (the disclosure of which is incorporated herein). In accordance with that process, it is possible to produce the desired cyano acid in the form of calcium salt by a facile procedure. Since the process of this invention can be applied directly to the reaction of the cyano acid in the form of the calcium salt, the over-all synthesis process can be simplified and the number of manipulative operations minimized by using the calcium 5-cyano-1-hydrocarbylpyrrole-2-acetate as a reactant in the present process. Hence, this constitutes another preferred embodiment of this invention.

Suitable 5-cyano-1-hydrocarbylpyrrole-2-acetic acids (which may be employed as free acids or as such salts as the sodium salt, potassium salt, lithium salt, or calcium salt) are exemplified by 5-cyano-1-methylpyrrole-2-acetic acid, 5-cyano-1-ethylpyrrole-2-acetic acid, 5-cyano-1-propylpyrrole-2-acetic acid, 5-cyano-1-amylpyrrole-2-acetic acid, 5-cyano-1-phenylpyrrole-2-acetic acid, 5-cyano-1-cyclohexylpyrrole-2-acetic acid, 5-cyano-1-benzylpyrrole-2-acetic acid, 5-cyano-1,3-dimethylpyrrole-2-acetic acid, 5-cyano-1,4-dimethylpyrrole-2-acetic acid, 5-cyano-1,3,4-trimethylpyrrole-2-acetic acid, and the like. It will of course be obvious that substituents in the two and/or three position of the pyrrole ring should be innocuous in the sense that they will not interfere with the desired reaction.

The aryl Grignard compound used in the process will, to a large extent, be dictated by the identity of the end product desired. A wide variety of Grignard compounds are entirely suitable for such use and methods for their synthesis are well known in the art. See for example, Kharasch and Reinmuth, "Grignard Reaction of Nonmetallic Substances," Prentice-Hall, New York, 1954, and "Metal-Organic Compounds," (Number 23 of the Advances in Chemistry Series), American Chemical Society, Washington, D.C. 1959, pages 73–81.

Because of the pharmacological efficacy and commercial utility of 5-cyano-1-methyl-p-toluoylpyrrole-2-acetic acid, a preferred Grignard reagent for use in the process is a p-tolyl Grignard reagent such as p-tolyl magnesium chloride, p-tolyl magnesium bromide, and p-tolyl magnesium iodide.

As in the case of the Kondo et al. process, preferably the Grignard reagent is used in an amount more than two molar equivalents relative to the 5-cyano-1-hydrocarbylpyrrole-2-acetic acid reactant. Normally, from about three to about five equivalents of the Grignard reagent will be employed although reasonable deviations from this range are permissible.

Reaction times are normally dependent to some extent on the temperature at which the reaction is performed. Normally, they will be within the range of about four hours or less although in some instances it may be desirable to conduct the reaction for a somewhat longer period. In most cases, however, the process of this invention may be effected in reaction times of about two hours or less.

Any conventional method for effecting the hydrolysis of the ketimine salt-containing reaction product may be utilized provided, of course, that the conditions are not so severe as to destroy the desired product. Suitable hydrolysis procedures as well as procedures for effecting the work-up of the product in connection with the hydrolysis procedure are set forth in the Kondo et al. application and the ensuing examples.

The practice and various features, advantages, and embodiments of this invention will become still further apparent from the following illustrative examples and the appended claims.

EXAMPLE 1

To a solution of the Grignard reagent prepared from 0.71 g. (31 mmol) of magnesium and 5.3 g. (31 mmol) of 4-bromotoluene in 20 ml. of anhydrous tetrahydrofuran was added under an atmosphere of nitrogen a solution of 0.98 g. (6.0 mmol) of 5-cyano-1-methylpyrrole-2-acetic acid in 5 ml. of tetrahydrofuran. After the resulting yellow suspension was heated to the boiling point, 20 g. of diphenyl ether was added, and tetrahydrofuran was distilled from the reaction mixture until the temperature reached 110° C. The reaction mixture was then heated under reflux (110° C.) for 1.5 hours. During this time, the color of the suspension changed from yellow to dark orange. The reaction mixture was cooled and partitioned between ether and dilute aqueous hydrochloric acid. The ether phase was extracted with five percent aqueous sodium hydroxide solution, which was then acidified and extracted with methylene chloride. The methylene chloride solution was dried over magnesium sulfate and concentrated to give 30 mg. of purple liquid which contained only a trace of starting cyanoacid by nmr analysis. The aqueous phase was heated in a steam bath for four hours, and the resulting suspension was cooled and extracted with methylene chloride. The methylene chloride solution was dried over magnesium sulfate and concentrated to give 1.33 g. (86% yield) of 1-methyl-5-p-toluoyl-pyrrole-2-acetic acid as a brown solid.

EXAMPLE 2

To a solution of the Grignard reagent prepared from 0.46 g. (20 mmol) of magnesium and 3.4 g. (20 mmol) of 4-bromotoluene in 15 ml. of anhydrous tetrahydrofuran was added under an atmosphere of nitrogen 1.12 g. (6.0 mmol) of the sodium salt of 5-cyano-1-methylpyrrole-2-acetic acid. To the resulting suspension was added 20 g. of diphenyl ether, and the reaction mixture was heated to remove tetrahydrofuran by distillation until the temperature reached 110° C. The reaction mixture was then successively heated under reflux at 110° C. for two hours, cooled, and partitioned between ether and dilute aqueous hydrochloric acid. The ether phase was worked up in the manner described in Example 1 to give 100 mg. (9%) of purple solid that contained mainly 5-cyano-1-methylpyrrole-2-acetic acid by nmr analysis. The aqueous phase was heated in a steam bath for 7 hours and the product was isolated after extraction with methylene chloride to give 1.15 g. (yield: 75%, 83% based on unrecovered cyanoacid) of 1-methyl-5-p-toluoylpyrrole-2-acetic acid as a brown solid.

EXAMPLE 3

To a solution of the Grignard reagent prepared from 0.82 g. (36 mmol) of magnesium and 6.2 g. (36 mmol) of 4-bromotoluene in 15 ml. of anhydrous tetrahydrofuran was added 1.2 g. of solid material which contained about 6.0 mmol of 5-cyano-1-methylpyrrole-2-acetate as the calcium salt and some water which persisted after drying in a vacuum oven. Diphenyl ether (20 g.) was added, and the reaction mixture was heated to remove tetrahydrofuran by distillation until the temperature reached 110° C. The reaction mixture was then heated under reflux for two hours, cooled, and partitioned between ether and dilute aqueous hydrochloric acid. Following a work-up procedure similar to that described for Example 1, there was obtained 130 mg. (13%) of 5-cyano-1-methylpyrrole-2-acetic acid and 970 mg. (yield: 63%, 73% based on unrecovered cyanoacid) of 1-methyl-5-p-toluoylpyrrole-2-acetic acid as brown solids.

EXAMPLE 4

To a solution of the Grignard reagent prepared from 0.71 g. (31 mmol) of magnesium and 5.3 g. (31 mmol) of 4-bromotoluene in a mixture of 20 ml. of anisole and 5 ml. of tetrahydrofuran was added over five minutes with stirring and heating a solution of 0.98 g. (6.0 mmol) of 5-cyano-1-methylpyrrole-2-acetic acid in a mixture of 5 ml. of anisole and 3 ml. of tetrahydrofuran. The reaction mixture was then heated under reflux (115° C.) for two hours, cooled, and partitioned between ether and dilute aqueous hydrochloric acid. Following a work-up procedure similar to that described for Example 1, there was obtained from the ether phase 60 mg. of purple liquid that contained only a trace of starting cyanoacid, and from the aqueous phase, 1.18 g. (77% yield) of 1-methyl-5-p-toluoylpyrrole-2-acetic acid as a brown solid.

From the above examples it can be seen that use of the solvent systems of this invention gives rise to the facile preparation of the desired product in good yields and short reaction times. The efficacy of the aromatic solvent systems of this invention becomes still further apparent from a consideration of the difficulties encountered in the ensuing comparative examples wherein high boiling aliphatic ether systems were employed.

EXAMPLE 5—COMPARATIVE

A solution of p-tolyl magnesium bromide (from 0.71 g., 31 mmol, of magnesium and 5.3 g., 31 mmol, of p-tolyl bromide) was prepared in a mixture of 10 ml. of tetrahydrofuran and 10 ml. of n-butyl ether. After tetrahydrofuran had been distilled from the mixture so that the boiling point was 110° C., a solution of 0.98 g. (6.0 mmol) of 5-cyano-1-methylpyrrole-2-acetic acid in 3 ml. of tetrahydrofuran and 3 ml. of n-butyl ether was added dropwise. A sticky, brown precipitate formed which did not disperse as in other successful reactions (cf. Examples 1–4 above), but which remained on the walls of the reaction vessel. No further reaction appeared to take place after continued refluxing of the reaction mixture.

EXAMPLE 6—COMPARATIVE

To a solution of p-tolyl magnesium bromide (prepared from 0.66 g., 29 mmol, of magnesium and 4.9 g., 29 mmol, of p-bromotoluene) in 15 ml. of tetrahydrofuran was added 15 ml. of diglyme (diethylene glycol dimethyl ether). The resulting solution was heated to 80° C. and a solution of 0.91 g. (5.6 mmol) of 5-cyano-1-methylpyrrole-2-acetic acid in 5 ml. of diglyme was added dropwise, forming a fine, yellow precipitate of the magnesium bromide salt of the acid. Tetrahydrofuran was distilled from the reaction mixture until the boiling point reached 110° C. The reaction mixture was then refluxed at 110°–115° C. for an additional 1.5 hours, cooled, and partitioned between diethyl ether and dilute aqueous HCl. The organic phase was washed several times with $H_2O$ and then extracted with five percent aqueous NaOH solution. After this extract had been washed with ether, acidified, and extracted with methylene chloride, the methylene chloride solution was dried and concentrated to leave a liquid which consisted mainly of diglyme but which also contained an undetermined amount of starting cyanoacid. The acidic aqueous phase was heated in a steam bath for five hours, and the precipitate was collected on a filter and dried to give 0.67 g. (47%) of 5-p-toluoyl-1-methylpyrrole-2-acetic acid as a gray solid.

The aromatic ether solvent systems of this invention may contain small, innocuous amounts of aliphatic ethers such as diglyme and like high boiling polyethers. However, for best results the system should be free of such materials.

I claim:

1. In a process for preparing 5-aroyl-1-hydrocarbylpyrrole-2-acetic acids characterized by reacting a 5-cyano-1-hydrocarbylpyrrole-2-acetic acid with an aryl Grignard compound and then hydrolyzing the resultant reaction product, the improvement pursuant to which the reaction between the 5-cyano-1-hydrocarbylpyrrole-2-acetic acid and the aryl Grignard compound is performed at a temperature above about 100° C. in a liquid ether reaction medium consisting essentially of an aromatic ether and, optionally, tetrahydrofuran or methyl tetrahydrofuran, or both.

2. A process in accordance with claim 1 characterized in that it is performed at a temperature in the range of about 100° to about 150° C.

3. A process in accordance with claim 1 characterized in that the aromatic ether is an aryl monoether.

4. In a process for preparing 5-aroyl-1-hydrocarbylpyrrole-2-acetic acids characterized by reacting a 5-cyano-1-hydrocarbylpyrrole-2-acetic acid with an aryl Grignard compound and then hydrolyzing the resultant reaction product, the improvement pursuant to which the reaction between the 5-cyano-1-hydrocarbylpyrrole-2-acetic acid and the aryl Grignard compound is performed at a temperature above about 100° C. in a liquid ether reaction medium consisting essentially of (i) an aromatic ether and (ii) tetrahydrofuran or methyl tetrahydrofuran, or both.

5. A process in accordance with claim 4 characterized in that it is performed at a temperature in the range of about 100° to about 150° C.

6. A process in accordance with claim 4 characterized in that said liquid ether reaction medium consists essentially of an aryl monoether and tetrahydrofuran.

7. A process in accordance with claim 4 characterized in that the reaction is performed under reflux at a temperature in the range of about 100° to about 150° C.

8. A process in accordance with claim 1 or claim 4 characterized by using more than two moles of the aryl Grignard compound per mole of the 5-cyano-1-hydrocarbylpyrrole-2-acetic acid.

9. A process in accordance with claim 1 or claim 4 characterized in that the 5-cyano-1-hydrocarbylpyrrole-2-acetic acid is 5-cyano-1-methylpyrrole-2-acetic acid.

10. A process in accordance with claim 1 or claim 4 characterized in that the 5-cyano-1-hydrocarbylpyrrole-2-acetic acid is introduced into the reaction mixture in the form of an alkali metal salt thereof.

11. A process in accordance with claim 1 or claim 4 characterized in that the 5-cyano-1-hydrocarbyl-2-acetic acid is introduced into the reaction mixture in the form of a calcium salt thereof.

12. A process in accordance with claim 4 characterized in that at the outset the aryl Grignard compound is synthesized in tetrahydrofuran or methyl tetrahydrofuran and the resultant reaction solution is employed in forming the reaction mixture in which the aryl Grignard compound and the 5-cyano-1-hydrocarbylpyrrole-2-acetic acid are reacted with each other.

13. A process in accordance with claim 4 characterized in that the aryl Grignard compound is a p-tolyl Grignard compound, in that the 5-cyano-1-hydrocarbylpyrrole-2-acetic acid is 5-cyano-1-methylpyrrole-2-acetic acid, in that more than two moles of the p-tolyl Grignard compound are used per mole of the 5-cyano-1-methylpyrrole-2-acetic acid, in that said ether reaction medium consists essentially of an aryl monoether and tetrahydrofuran, and in that the reaction is performed at a temperature within the range of about 100° to about 150° C.

14. A process in accordance with claim 4 characterized in that the aryl Grignard compound is a p-tolyl Grignard compound, in that the 5-cyano-1-hydrocarbylpyrrole-2-acetic acid is sodium 5-cyano-1-methylpyrrole-2-acetate, in that more than two moles of the p-tolyl Grignard compound are used per mole of the sodium 5-cyano-1-methylpyrrole-2-acetate, in that said ether reaction medium consists essentially of an aryl monoether and tetrahydrofuran, and in that the reaction is performed at a temperature within the range of about 100° to about 150° C.

15. A process in accordance with claim 4 characterized in that the aryl Grignard compound is a p-tolyl Grignard compound, in that the 5-cyano-1-hydrocarbylpyrrole-2-acetic acid is calcium 5-cyano-1-methylpyrrole-2-acetate, in that more then two moles of the p-tolyl Grignard compound are used per mole of the calcium 5-cyano-1-methylpyrrole-2-acetate, in that said ether reaction medium consists essentially of an aryl monoether and tetrahydrofuran, and in that the reaction is performed at a temperature within the range of about 100° to about 150° C.

16. A process in accordance with claim 1 wherein said aromatic ether is diphenyl ether or anisole.

17. A process in accordance with claim 4 wherein said aromatic ether is diphenyl ether or anisole.

18. A process in accordance with claim 13 wherein said monoether is diphenyl ether or anisole.

19. A process in accordance with claim 14 wherein said monoether is diphenyl ether or anisole.

20. A process in accordance with claim 15 wherein said monoether is diphenyl ether or anisole.

21. In a process for preparing 1-methyl-5-p-toluoylpyrrole-2-acetic acid characterized by reacting 5-cyano-1-methylpyrrole-2-acetic acid with a p-tolyl Grignard compound and then hydrolyzing the resultant reaction product, the improvement pursuant to which the reactant between the 5-cyano-1-methylpyrrole-2-acetic acid and the p-tolyl Grignard compound is performed at a temperature above about 100° C. in a liquid ether reaction medium consisting essentially of an aromatic ether.

22. A process in accordance with claim 21 characterized in that it is preformed at a temperature in the range of about 100° to about 150° C. and in that more than 2 moles of the p-tolyl Grignard compound are used per mole of the 5-cyano-1-methylpyrrole-2-acetic acid.

* * * * *

UNITED STATES PATENT AND TRADEMARK OFFICE
CERTIFICATE OF CORRECTION

PATENT NO. : 4,246,176
DATED : January 20, 1981
INVENTOR(S) : Edward J. Zaiko

It is certified that error appears in the above-identified patent and that said Letters Patent are hereby corrected as shown below:

Column 10, line 16, reads "preformed", should read
-- performed --.

Title page, under "References Cited", top of second
column reads in part "Non-Mettalic", should
read -- "Nonmetallic" --.

Column 8, line 39, reads "5-cyano-1-hydrocarbyl-2-",
should read --  5-cyano-1-hydrocarbylpyrrole-2-  --.

Column 9, line 7, reads "more then", should read
-- more than --.

Signed and Sealed this

Twenty-eighth Day of April 1981

[SEAL]

Attest:

RENE D. TEGTMEYER

Attesting Officer     Acting Commissioner of Patents and Trademarks